United States Patent [19]
Perrella et al.

[11] 3,944,544
[45] Mar. 16, 1976

[54] BIS-CEPHALOSPORINS

[75] Inventors: Donald J. Perrella, Princeton Junction, N.J.; Joseph E. Dolfini, Cincinnati, Ohio

[73] Assignee: E. R. Squibb & Sons, Inc., Princeton, N.J.

[22] Filed: May 30, 1974

[21] Appl. No.: 474,731

Related U.S. Application Data

[62] Division of Ser. No. 291,442, Sept. 22, 1972, Pat. No. 3,825,536.

[52] U.S. Cl. ............................ 260/243 C; 424/246
[51] Int. Cl.² .................................... C07D 501/20
[58] Field of Search ............................... 260/243 C

[56] References Cited
UNITED STATES PATENTS 3,825,536   7/1974   Perrella et al.................. 260/243 C

*Primary Examiner*—Nicholas S. Rizzo
*Attorney, Agent, or Firm*—Lawrence S. Levinson; Merle J. Smith; Stephen B. Davis

[57] ABSTRACT

Derivatives of difunctional compounds such as dicarboxylic acids, diisocyanates or diisothiocyanates wherein each functional group is reacted with 7-aminocephalosporanic acid or 7-aminodesacetoxycephalosporanic acid possess antibacterial activity.

7 Claims, No Drawings

BIS-CEPHALOSPORINS

RELATED APPLICATION

This application is a division of copending application Serial No. 291,442, filed Sept. 22, 1972, now U.S. Pat. No. 3,825,536.

The present invention relates to antibacterial agents, and more particularly, to antibacterial agents containing at least two antibacterial moieties.

It is an object of the present invention to provide new antibacterial agents. Another object is to provide antibacterial agents of improved efficacy. A further object is to provide antibacterial agents which contain at least two antibacterial moieties. Still another object is to provide antibacterial agents from di- or higher polyfunctional compounds. These and other objects of the present invention will be apparent as the description proceeds.

SUMMARY OF THE INVENTION

The antibacterial agents of the present invention comprise derivatives of di- or higher polyfunctional compounds such as di- or higher polycarboxylic acids or di- or higher polyisocyanates or isothiocyanates wherein at least two functional groups are reacted with 7-aminocephalosporanic acid (7-ACA) or 7-aminodesacetoxycephalosporanic acid (7-ADCA).

DETAILED DESCRIPTION

The di- or higher polyfunctional starting compounds of the present invention comprise di- or higher polycarboxylic acids or di- or higher polyisocyanates or di- or higher polyisothiocyanates. At least two functional groups of the starting compound are reacted with the same or different antibacterial moiety. The antibacterial moieties of the present invention comprise 7-ACA or 7ADCA or derivatives thereof. By way of illustration, each carboxyl group of a dicarboxylic acid may be reacted with the amino group of 7-ACA or 7-ADCA, or one carboxyl group reacted with the amino group of 7-ACA and one carboxyl group reacted with the amino group of 7-ADCA.

In the case of a diisocyanate, each isocyanate group may be reacted with the amino group of 7-ACA or 7-ADCA or one isocyanate group may be reacted with the amino group of 7-ACA and one isocyanate group reacted with the amino group of 7-ADCA.

Various types of polyfunctional compounds may be used in the present invention. The polyfunctional compound may be aliphatic, alicyclic, aromatic or heterocyclic. By way of illustration, some examples for each group follow.

I. POLYBASIC ACIDS

1. Aliphatic acids — oxalic, fumaric, malonic, maleic, succinic, tartaric, glutaric, adipic, pimelic, suberic, azelaic, sebacic, etc.
2. Alicyclic acids — tetrahydrophthalic, hexahydrophthalic, endomethylenetetrahydrophthalic, camphoric, etc.
3. Aromatic acids — phthalic, isophthalic, terephthalic, hemimellitic, trimellitic, trimesic, pyromellitic, homophthalic, o-phenyleneacetic-β-propionic acid, etc.
4. Heterocyclic acids - pyridine-3,4-dicarboxylic acid, quinolinic acid, γ-pyran-2,6-dicarboxylic acid, chelidonic acid, pyridine-2,3,4-tricarboxylic acid, thiophene-2,5-dicarboxylic acid, etc.

It will be understood by those skilled in the art that the polycarboxylic acid may be reacted as such or in the form of its acyl anhydride, activated ester, acyl halide, i.e., the acyl chloride or acyl bromide, etc.

II. DIISOCYANATES

1. Aliphatic isocyanates — ethylene diisocyanate, propylene-1,2-diisocyanate, butylene-1,3-diisocyanate, tetramethylene diisocyanate, pentamethylene diisocyanate, hexamethylene diisocyanate, 1,2,4-butane triisocyanate, etc., and the corresponding isothiocyanates;
2. Aromatic isocyanates — p-phenylene diisocyanate, 2,4-tolylenediisocyanate, 2,4-chlorophenylene diisocyanate, 2,6-tolylenediisocyanate, diphenyl-4,4'-diisocyanate, p-isocyanatobenzyl isocyanate, diphenylmethane-4,4'-diisocyanate, 3,3'-bitolylene-4,4'-diisocyanate, 3,3'-dimethyldiphenylmethane-4,4'-diisocyanate, 1,2,4-benzene triisocyanate, 1,2,5-benzene triisocyanate, etc., and the corresponding isothiocyanates;
3. Alicyclic isocyanates — 1,2-diisocyanocyclohexane, 1,3-diisocyanocyclohexane, 1,4-diisocyanocyclohexane, cyclopentyl-1,3-diisocyanate, etc., and the corresponding isothiocyanates;
4. Heterocyclic isocyanates — pyridine-2,6-diisocyanate, furan-2,5-diisocyanate, thiophene-2,4-diisocyanate, thiophene-2,5-diisocyanate, pyrimidine-4,6-diisocyanate, pyrimidine-4,5,6-triisocyanate, etc., and the corresponding isothiocyanates.

The compounds of the present invention include the free acids as well as physiologically acceptable metal salts, esters, or salts of physiologically acceptable organic bases. Examples of suitable metal salts include the alkali metal and alkaline earth metal salts, e.g., the Na, K, Mg and Ca. The ammonium ion may be included among the alkali metals. Examples of suitable esters include radicals derived from alcohols of up to 7 carbon atoms, e.g., methyl, propyl, t-butyl, trichloroethyl, pivaloyloxymethyl, benzyl, p-nitrophenyl, trimethyl silyl, trimethyl stannyl, methoxymethyl, and the like. Examples of suitable bases include substituted ammonium salts, e.g., salts of nontoxic amines such as trialkylamines, including triethylamine, procaine, dibenzylamine, N-benzyl-β-phenethylamine, N,N'-dibenzylethylenediamine, N-(lower)-alkylpiperidine, e.g., N-ethylpiperidine and other amines which have been used to form salts with benzylpenicillin and the like. The foregoing metal salts or organic bases and esters are prepared according to known techniques.

The compounds of this invention form salts which are also part of the invention. Basic salts form with the carboxyl group of the 7-ACA or 7-ADCA moiety. It is frequently convenient to isolate and purify the product by forming a soluble or insoluble salt, as desired, then regenerating the free compound, by neutralization for example.

The compounds of this invention have a broad spectrum of antibacterial activity against both gram positive and gram negative organisms such as *Staphylococcus aureus, Salmonella schottmuelleri, Pseudomonas aeruginosa, Proteus vulgaris, Escherichia coli* and *Streptococcus pyogenes*. They may be used as antibacterial agents in a prophylactic manner, e.g., in cleaning or disinfecting compositions, or otherwise to combat infections due to organisms such as those named above, and in general may be utilized in a manner similar to penicillin G and other penicillins and cephalosporins. For example, a compound of the invention or a physiologically acceptable salt thereof may be used in various animal species in an amount of about 0.1 to 100 mg/kg daily, orally or parenterally, in single or two to four divided doses to treat infections of bacterial origin. Up to about 600 mg of a compound of the invention or a salt thereof may be incorporated in an oral dosage form such as tablets, capsules or elixirs or in an injectable form in a sterile aqueous vehicle prepared according to conventional pharmaceutical practice. In cleaning or disinfecting compositions, e.g., in barns or dairy equipment, a concentration of about 0.01 to 1% by weight of such compounds admixed with, suspended or dissolved in conventional inert dry or aqueous carriers for application by washing or spraying may be used.

The compounds of the present invention may be readily prepared by reacting either 7-ACA or 7-ADCA, the carboxyl group of which is protected, with an acyl dihalide, or an isocyanate or an isothiocyanate. The reaction takes place in an inert solvent such as, for example, chloroform, benzene, toluene, ethylene chloride, methylene chloride, dioxane, nitromethane, acetonitrile, dimethylformamide or diethyl ether, or mixtures of the foregoing solvents. The carboxyl group of either the 7-ACA or 7-ADCA moiety may be protected by any convenient ester group which will not interfere with reaction between the amino group of either the 7-ACA or 7-ADCA moiety and either the acyl halide or isocyanate compound. The reaction takes place at temperatures in the range of from about −30°C to about 20°C.

While examples of specific polycarboxylic acids and polyisocyanates or polyisothiocyanates have been given previously, it is to be understood that any polycarboxylic acid, polyisocyanate or polyisothiocyanate may be employed according to the present invention provided no substituents are present which would interfere with the reaction with the antibacterial moiety. With the foregoing understanding, the following paragraphs described preferred compounds.

The aliphatic polycarboxylic acids, examples of which have been given previously, comprise polyalkanoic or polyalkenoic acids of from 2 to about 12 carbon atoms (including those in the carboxyl groups). The acid may be substituted, e.g., by a halogen.

The alicyclic polycarboxylic acids, examples of which have been given previously, comprise cycloalkyl or cycloalkenyl compounds of 5 or 6 carbon atoms in the ring, and a total of from 7 to about 10 carbon atoms (including those in the carboxyl groups), or a bicyclic ring system having a total of about 9 carbon atoms (including those in the carboxyl groups).

The aromatic polycarboxylic acids, examples of which have been given previously, comprise benzene polycarboxylic acids having from 8 to 10 carbon atoms, or homologs thereof having from 9 to about 12 carbon atoms (including those in the carboxyl groups).

The heterocyclic polycarboxylic acids, examples of which have been given previously, comprise 5- or 6-membered rings containing a single heteroatom which may be N, O or S, and having a total of 4 to 8 carbon atoms (including those in the carboxyl groups).

The aliphatic polyisocyanates or polyisothiocyanates, examples of which have been given previously, comprise polyisocyanates or polyisothiocyanates of from 2 to about 10 carbon atoms (including those in the isocyanate or isothiocyanate groups).

The aromatic polyisocyanates or polyisothiocyanates, examples of which have been given previously, comprise benzene or benzyl polyisocyanates or polyisothiocyanates of from 8 to about 10 carbon atoms (including those in the isocyanate or isothiocyanate groups) or a benzene isocyanate or isothiocyanate joined directly or through a methylene group to a second benzene isocyanate or isothiocyanate, respectively, in which case the compound has from 14 to about 17 carbon atoms (including those in the isocyanate or isothiocyanate groups). The benzene rings may be substituted, e.g., by a halogen atom, or by methyl groups as long as the upper limits of carbon atoms are not exceeded.

The alicyclic polyisocyanates or polyisothiocyanates, examples of which have been given previously, comprise cycloalkyl compounds of 5 or 6 carbon atoms in the ring which carbons may be substituted by a methyl group or by a halogen, and which compounds have a total of from 7 to about 10 carbon atoms (including those in the isocyanate or isothiocyanate groups).

The heterocyclic isocyanates or isothiocyanates, examples of which have been given previously, comprise 5- or 6-membered rings containing a single heteroatom which may be N, O, or S, or two nitrogen heteroatoms, and which have a total of from 6 to about 8 carbon atoms (including those in the isocyanate or isothiocyanate groups).

The following examples illustrate the present invention without, however, limiting the same thereto. All temperatures are expressed in degrees Celsius.

EXAMPLE 1

N,N′-Oxalylbis[7-Aminocephalosporanic Acid]

A solution of 7-aminocephalosporanic acid (2 mmole) and triethylamine (4 mmole) in 25 mg of pure chloroform is cooled to −10°C. Trimethylsilyl chloride (4 mmole) is then added over a 10-minute interval. The resulting mixture is stirred for about 30 minutes more. Triethylamine (2 mmoles) is again added followed by a solution of oxalyl chloride (1 mmole) in 10 ml of pure chloroform added over a 10-minute interval, the temperature being maintained at −10°C. After an additional 1 hour of stirring at this temperature, the reaction mixture is poured into cold water and the pH adjusted to about 3.5. The chloroform layer containing the product is separated. This organic layer is then layered with water and the pH of the aqueous layer adjusted to pH 7.5 with dilute sodium hydroxide with vigorous shaking of the mixture. The chloroform layer is drawn off and the aqueous solution of the product is layered with ethyl acetate. The pH of the aqueous solution is lowered to 3.5; the ethyl acetate layer is washed with water and saturated aqueous sodium chloride. After drying and evaporating the ethyl acetate layer, the title compound is obtained.

EXAMPLE 2

N,N′-Succinoylbis[7-Aminocephalosporanic Acid]

Following the procedure of Example 1 but substituting 1 mmole of succinoyl chloride in place of oxalyl chloride, the title compound is obtained.

EXAMPLE 3

N,N'-Adipoylbis[7-Aminocephalosporanic Acid]

Following the procedure of Example 1 but substituting 1 mmole of adipoyl chloride in place of oxalyl chloride, the title compound is obtained.

EXAMPLE 4

N,N'-Sebacoylbis[7-Aminocephalosporanic Acid]

Following the procedure of Example 1 but substituting 1 mmole of sebacoyl chloride in place of oxalyl chloride, the title compound is obtained.

EXAMPLE 5

N,N'-Terephthaloylbis[7-Aminocephalosporanic Acid]

Following the procedure of Example 1 but substituting 1 mmole of terephthaloyl chloride in place of oxalyl chloride, the title compound is obtained.

EXAMPLE 6

N,N'-Isophthaloylbis[7-Aminocephalosporanic Acid]

Following the procedure of Example 1 but substituting 1 mmole of isophthaloyl chloride in place of oxalyl chloride, the title compound is obtained.

EXAMPLE 7

N,N'-Phthaloylbis[7-Aminocephalosporanic Acid]

Following the procedure of Example 1 but substituting 1 mmole of phthaloyl chloride in place of oxalyl chloride, the title compound is obtained.

EXAMPLE 8

N,N'-Tetrahydrophthaloylbis[7-Aminocephalosporanic Acid]

Following the procedure of Example 1 but substituting 1 mmole of tetrahydrophthaloyl chloride in place of oxalyl chloride, the title compound is obtained.

EXAMPLE 9

N,N'-Endomethylenetetrahydrophthaloylbis[7-Aminocephalosporanic Acid]

Following the procedure of Example 1 but substituting 1 mmole of endomethylenetetrahydrophthaloyl chloride in place of oxalyl chloride, the title compound is obtained.

EXAMPLE 10

N,N'-Camphoroylbis[7-Aminocephalosporanic Acid]

Following the procedure of Example 1 but substituting 1 mmole of camphoroyl chloride in place of oxalyl chloride, the title compound is obtained.

EXAMPLE 11

N,N'-(3,4-Pyridinedicarbonyl)-bis-[7-Aminocephalosporanic Acid]

Following the procedure of Example 1 but substituting 1 mmole of 3,4-pyridinedicarbonyl chloride in place of oxalyl chloride, the title compound is obtained.

EXAMPLE 12

N,N'-Quinolinoylbis[7-Aminocephalosporanic Acid]

Following the procedure of Example 1 but substituting 1 mmole of quinolinoylbis chloride in place of oxalyl chloride, the title compound is obtained.

EXAMPLE 13

Ethylenediamine-bis-N,N'-(7-Carbonylaminocephalosporanic Acid)

Following the procedure of Example 1 but substituting 1 mmole of ethylenediisocyanate for oxalyl chloride, the title compound is obtained.

EXAMPLE 14

1,4-Phenylenediamine-bis-N,N'-(7-Carbonylaminocephalosporanic Acid)

Following the procedure of Example 1 but substituting 1 mmole of 1,4-phenylenediisocyanate for oxalyl chloride, the title compound is obtained.

EXAMPLE 15

1,4-Cyclohexyldiamine-bis-N,N'-(7-Carbonylaminocephalosporanic Acid)

Following the procedure of Example 1 but substituting 1 mmole of 1,4-cyclohexyldiisocyanate for oxalyl chloride, the title compound is obtained.

EXAMPLES 16–30

Following the procedure of Examples 1 but substituting 7-aminodesacetoxycephalosporanic acid for 7-aminocephalosporanic acid in Examples 1–15, the following compounds are obtained:

| Example | Compound |
|---|---|
| 16 | N,N'-oxalylbis[7-aminodesacetoxycephalosporanic acid] |
| 17 | N,N'-succinoylbis[7-aminodesacetoxycephalosporanic acid] |
| 18 | N,N'-adipoylbis[7-aminodesacetoxycephalosporanic acid] |
| 19 | N,N'-sebacoylbis[7-aminodesacetoxycephalosporanic acid] |
| 20 | N,N'-terephthaloylbis[7-aminodesacetoxycephalosporanic acid] |
| 21 | N,N'-isophthaloylbis[7-aminodesacetoxycephalopsoranic acid] |
| 22 | N,N'-phthaloylbis[7-aminodesacetoxycephalosporanic acid] |
| 23 | N,N'-tetrahydrophthaloylbis[7-aminodesacetoxycephalosporanic acid] |
| 24 | N,N'-endomethylenetetrahydrophthaloylbis-[7-aminodesacetoxycephalosporanic acid] |
| 25 | N,N'-camphoroylbis[7-aminodesacetoxycephalosporanic acid] |
| 26 | N,N'-(3,4-pyridinedicarbonyl)-bis-[7-aminodesacetoxycephalosporanic acid] |
| 27 | N,N'-quinolinoylbis[7-aminodesacetoxycephalosporanic acid] |
| 28 | ethylenediamine-bis-N,N'-(7-carbonylaminodesacetoxycephalosporanic acid) |
| 29 | 1,4-phenylenediamine-bis-N,N'-(7-carbonylaminodesacetoxycephalosporanic acid) |
| 30 | 1,4-cyclohexyldiamine-bis-N,N'-(7-carbonylaminodesacetoxycephalosporanic acid) |

EXAMPLE 31

2,6-Pyridyldiamine-bis-N,N'-(7-Carbonylaminocephalosporanic Acid)

Following the procedure of Example 1 but substituting 1 mmole of pyridine-2,6-diisocyanate for oxalyl chloride, the title compound is obtained.

EXAMPLES 32–53

Following the procedure of Example 1 but substituting for oxalyl chloride 1 mmole of the compound in Column I, there is obtained a compound of the following formula

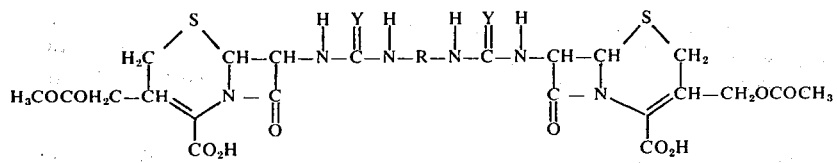

wherein R is the radical indicated in Column II and Y is as indicated in Column III.

| Example | I | II | III |
|---|---|---|---|
| 32 | Propylene-1,2-diisothiocyanate | $-CH_2CH_2CH_2-$ | S |
| 33 | Butylene-1,3-diisocyanate | $-CH_2CH_2CH_2-$ with $CH_3$ | O |
| 34 | Tetramethylene diisocyanate | $-CH_2CH_2CH_2CH_2-$ | S |
| 35 | Pentamethylene diisocyanate | $-CH_2(CH_2)_3CH_2-$ | O |
| 36 | Hexamethylene diisothiocyanate | $-CH_2(CH_2)_4CH_2-$ | S |
| 37 | p-Phenylene diisothiocyanate | p-phenylene | S |
| 38 | 2,4-Tolylene diisocyanate | 2,4-tolylene ($CH_3$) | O |
| 39 | 2,4-Chlorophenylene diisocyanate | 2,4-chlorophenylene (Cl) | O |
| 40 | 2,6-Tolylene diisothiocyanate | 2,6-tolylene ($CH_3$) | S |
| 41 | Diphenyl-4,4'-diisocyanate | biphenyl | O |
| 42 | p-Isocyanatobenzyl isocyanate | phenyl-$CH_2-$ | O |
| 43 | Diphenylmethane 4,4'-diisocyanate | phenyl-$CH_2-$phenyl | O |
| 44 | Diphenylmethane-4,4'-diisothiocyanate | phenyl-$CH_2-$phenyl | S |
| 45 | 3,3'-Dimethyldiphenylmethane-4,4'-diisocyanate | ($CH_3$)phenyl-$CH_2-$phenyl($CH_3$) | O |
| 46 | 3,3'-Bitolylene-4,4'-diisocyanate | ($H_3C$)phenyl-phenyl($CH_3$) | O |
| 47 | Cyclohexane-1,2-diisocyanate | cyclohexane | O |

| Example | I | II | III |
|---|---|---|---|
| 48 | Cyclohexane-1,3-diisothiocyanate |  | S |
| 49 | Cyclopentyl-1,3-diisocyanate |  | O |
| 50 | Furan-2,5-diisocyanate |  | O |
| 51 | Thiophene-2,4-diisocyanate |  | O |
| 52 | Thiophene-2,5-diisothiocyanate |  | S |
| 53 | Pyrimidine-4,6-diisocyanate |  | O |

EXAMPLE 54

1,2,4-Benzene-tris-N,N',N''-(7-Carbonylaminocephalosporanic Acid)

Following the procedure of Example 1 but substituting 0.67 mmole of 1,2,4-benzene triisocyanate for oxalyl chloride, the title compound is obtained.

EXAMPLE 55

4,5,6-Pyrimidine-tris-N,N', N''-(7-Carbonylaminocephalosporanic Acid)

Following the procedure of Example 1 but substituting 0.67 mmole of pyrimidine-4,5,6-triisocyanate for oxalyl chloride, the title compound is obtained.

EXAMPLE 56

Succinoyl N-(7-Aminodesacetoxycephalosporanic Acid)-N'-(7-Aminocephalosporanic Acid)

A solution of 1 mmole of 7-ADCA and 2 mmoles of triethylamine in 30 ml of pure chloroform at ambient temperature is treated with 1 mmole of pure trimethylsilyl chloride. After stirring for 1 hour, 1 mmole of succinic anhydride is added with 1 mmole of additional triethylamine. The mixture is stirred for about 1 hour. After chilling to 0°C, 1 mmole of ethyl chloroformate is then added. After 15 minutes a solution of 1 mmole of 7-ACA and 2 mmoles of triethylamine in chloroform is added. The coolant is then removed and the reaction allowed to proceed for 1 hour. The reaction is then diluted with an equal volume of chloroform and extracted with several portions of cold 0.1 N aqueous hydrochloric acid, then washed with water. The organic solution is extracted with several volumes of pH 7.5 phosphate buffer. The aqueous extract is then acidified to about pH 3.5 and extracted with several volumes of ethyl acetate. The ethyl acetate extract is washed with water, then dried (Na$_2$SO$_4$) and evaporated at reduced pressure to deposit the title compound.

EXAMPLES 57–60

Following the procedure of Example 56 but substituting for succinic anhydride one mole of the compound listed in Column I, the product obtained is indicated in Column II.

| Example | I | II |
|---|---|---|
| 57 | Terephthalic acid | Terephthaloyl N-(7-aminodesacetoxycephalosporanic acid)-N'-(7-aminocephalosporanic acid) |
| 58 | Hexahydrophthalic acid | Hexahydrophthaloyl N-(7-aminodesacetoxycephalosporanic acid)-N'-(7-aminocephalosporanic acid) |
| 59 | λ-pyran-2,6-dicarboxylic acid | λ-pyran-2,6-dioyl N-(7-aminodesacetoxycephalosporanic acid)-N'-(7-aminocephalosporanic acid) |
| 60 | Thiophene-2,5-dicarboxylic acid | Thiophene-2,5-dioyl N-(7-aminodesacetoxycephalosporanic acid)-N'-(7-aminocephalosporanic acid) |

What is claimed is:

1. A compound of the formula:

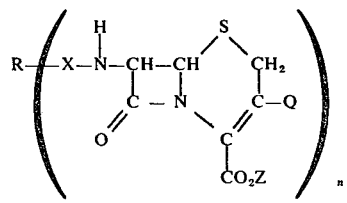

wherein R is furyl or thienyl; X is

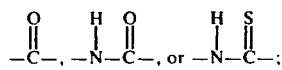

Q is —CH₃ or —CH₂OCOCH₃; Z is hydrogen, an alkali metal salt, an alkaline earth metal salt, NH₄, alkyl of 1 to 4 carbons, trichloroethyl, pivaloyloxymethyl, benzyl, p-nitrophenyl, trimethylsilyl, trimethylstannyl, methoxymethyl, triethylamine, procaine, dibenzylamine, N-benzyl-β-phenethylamine, N,N-dibenzylethylenediamine, or N-ethylpiperidine; and n is 2, 3 or 4.

2. A compound of claim 1 wherein X is

Q is —CH₃ and n is 2.

3. A compound of claim 1 wherein X is

Q is —CH₂OCOCH₃ and n is 2.

4. A compound of claim 1 wherein X is

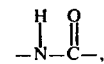

Q is —CH₃ and n is 2.

5. A compound of claim 1 wherein X is

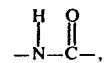

Q is —CH₂OCOCH₃ and n is 2.

6. A compound of claim 1 wherein X is

Q is —CH₃ and n is 2.

7. A compound of claim 1 wherein X is

Q is —CH₂OCOCH₃ and n is 2.

* * * * *

UNITED STATES PATENT AND TRADEMARK OFFICE
CERTIFICATE OF CORRECTION

PATENT NO. : 3,944,544
DATED : March 16, 1976
INVENTOR(S) : Donald J. Perrella et al.

It is certified that error appears in the above-identified patent and that said Letters Patent are hereby corrected as shown below:

Col. 1, line 39, "7ADCA" should read --7-ADCA--.

Col. 10, example 59, Cols. I and II, "$\lambda$" should read --$\gamma$--.

Signed and Sealed this twenty-second Day of June 1976

[SEAL]

Attest:

RUTH C. MASON
*Attesting Officer*

C. MARSHALL DANN
*Commissioner of Patents and Trademarks*